(12) United States Patent
Marcelli

(10) Patent No.: US 9,987,129 B2
(45) Date of Patent: Jun. 5, 2018

(54) HEART VALVE PROSTHESIS WITH INTEGRATED ELECTRONIC CIRCUIT FOR MEASURING INTRAVALVULAR ELECTRICAL IMPEDANCE, AND SYSTEM FOR MONITORING FUNCTIONALITY OF THE PROSTHESIS

(71) Applicant: ALMA MATER STUDIORUM—UNIVERSITÀ DI BOLOGNA, Bologna (IT)

(72) Inventor: Emanuela Marcelli, Bologna (IT)

(73) Assignee: ALMA MATER STUDIORUM—UNIVERSITÀ DI BOLOGNA, Bologna (IT)

( * ) Notice: Subject to any disclaimer, the term of this patent is extended or adjusted under 35 U.S.C. 154(b) by 52 days.

(21) Appl. No.: 15/303,414

(22) PCT Filed: Apr. 15, 2015

(86) PCT No.: PCT/EP2015/058201
§ 371 (c)(1),
(2) Date: Oct. 11, 2016

(87) PCT Pub. No.: WO2015/158789
PCT Pub. Date: Oct. 22, 2015

(65) Prior Publication Data
US 2017/0027689 A1    Feb. 2, 2017

(30) Foreign Application Priority Data
Apr. 16, 2014 (IT) .............................. BO2014A0217

(51) Int. Cl.
*A61F 2/24* (2006.01)
*A61B 5/00* (2006.01)
(Continued)

(52) U.S. Cl.
CPC .......... *A61F 2/2403* (2013.01); *A61B 5/0031* (2013.01); *A61B 5/02028* (2013.01);
(Continued)

(58) Field of Classification Search
CPC ......... A61F 2/24; A61F 2/2412; A61F 2/2418
(Continued)

(56) References Cited

U.S. PATENT DOCUMENTS

| 4,730,619 A | 3/1988 | Koning et al. |
| 5,487,760 A * | 1/1996 | Villafana ............. A61B 5/0031 |
| | | 607/119 |

(Continued)

FOREIGN PATENT DOCUMENTS

| WO | WO8705203 | 9/1987 |
| WO | WO2010062223 | 11/2008 |

OTHER PUBLICATIONS

International Search Report and Written Opinion for International Application No. PCT/EP2015/058201; Jun. 25, 2015, 9 pages.

*Primary Examiner* — Suzette J Gherbi
(74) *Attorney, Agent, or Firm* — Stetina Brunda Garred and Brucker

(57) ABSTRACT

A heart valve prosthesis of any type, with internal microelectronic circuit for monitoring the movement of the valve leaflets or of the movable opening and closing elements of said heart valve prosthesis, and external electronic system for telemetric monitoring of such a sensorized heart valve prosthesis, characterized in that said heart valve prosthesis comprises two or more electrodes set in the annular base body of the prosthesis itself, and comprises an internal microelectronic circuit, which is connected to electric power supply means, is equipped with means for generating, between said electrodes, an electrical field, the field lines of which are oriented so as to interfere with the opening and (Continued)

closing movement of the movable elements of said heart valve prosthesis or of the natural leaflets of the heart valve on which said prosthesis will be mounted, and is equipped with or connected to means for detecting the variations of said electrical field produced by the cyclic movement of opening or closing of said leaflets or of said movable elements, which will be expressed as variations of intravalvular electrical impedance and characterized in that it comprises, implanted, a transceiver unit with corresponding antenna for telemetric transmission of the data correlated to said variations of intravalvular electrical impedance, to an external unit that processes the collected data and uses them at least for purposes of diagnosis and prevention.

8 Claims, 4 Drawing Sheets

(51) Int. Cl.
 *G06F 19/00* (2018.01)
 *A61B 5/02* (2006.01)
 *A61B 5/053* (2006.01)
(52) U.S. Cl.
 CPC .......... *A61B 5/0538* (2013.01); *A61B 5/4836* (2013.01); *A61B 5/686* (2013.01); *A61B 5/6869* (2013.01); *A61B 5/7246* (2013.01); *A61B 5/7282* (2013.01); *G06F 19/3418* (2013.01); *A61F 2250/0002* (2013.01); *A61F 2250/0096* (2013.01)

(58) Field of Classification Search
 USPC .............................. 623/2.1–2.18, 2.36–2.42
 See application file for complete search history.

(56) References Cited

U.S. PATENT DOCUMENTS

| | | | |
|---|---|---|---|
| 5,792,194 A | 8/1998 | Morra | |
| 5,902,325 A | 5/1999 | Condie et al. | |
| 6,318,375 B1* | 11/2001 | Plicchi ................ | A61B 5/0422 128/899 |
| 7,089,051 B2 | 8/2006 | Javerud et al. | |
| 7,643,879 B2 | 1/2010 | Shuros et al. | |
| 2006/0009804 A1 | 1/2006 | Penderson | |
| 2011/0202129 A1* | 8/2011 | Fofsell ................ | A61B 5/6846 623/2.17 |
| 2012/0296382 A1 | 11/2012 | Shuros et al. | |
| 2016/0045312 A1* | 2/2016 | Braido ................ | A61B 5/6862 623/2.37 |
| 2017/0258585 A1* | 9/2017 | Marquez ............... | A61F 2/2409 |

* cited by examiner

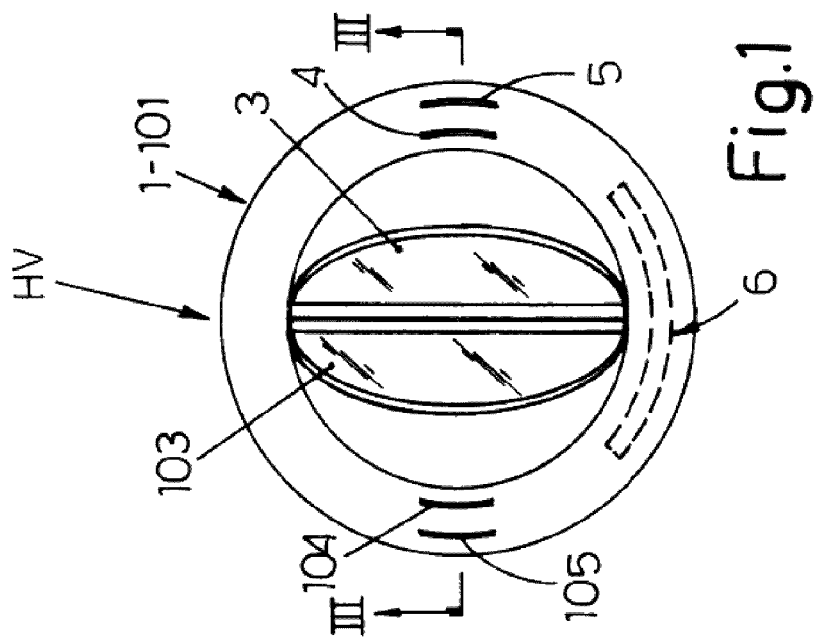
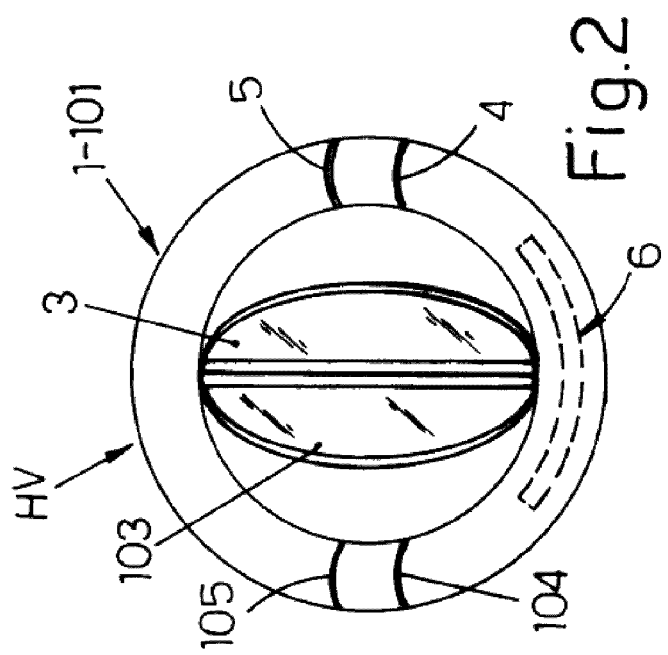

HEART VALVE PROSTHESIS WITH INTEGRATED ELECTRONIC CIRCUIT FOR MEASURING INTRAVALVULAR ELECTRICAL IMPEDANCE, AND SYSTEM FOR MONITORING FUNCTIONALITY OF THE PROSTHESIS

CROSS-REFERENCE TO RELATED APPLICATIONS

The present application claims priority to PCT International Application No. PCT/EP2015/058201 filed on Apr. 15, 2015, which application claims priority to Italian Patent Application No. BO2014A000217 filed Apr. 16, 2014, the entirety of the disclosures of which are expressly incorporated herein by reference.

STATEMENT RE: FEDERALLY SPONSORED RESEARCH/DEVELOPMENT

Not Applicable.

BACKGROUND

The invention relates to implantable cardiovascular devices and more in particular to cardiac-valve prosthetic devices that fall within the IPC (International Patent Classification) A61F2/24. There exist various prosthetic devices for correcting defects of heart valves, from simple annuloplasty rings, to be integrated in the natural heart valves of the patient for re-establishing proper functionality thereof, to valve prostheses proper that altogether replace the natural heart valves and that may be of a mechanical type (MHV), of a tissue type (THV), or a transcatheter tissue type (TAVI).

After implantation, the state of operation of heart valve prostheses, of whatever type, is currently being monitored with periodic follow-up and with imaging systems, at specialised health structures, in so far as, in tissue valve prostheses there may occur alterations of the valve leaflets owing to calcification phenomena, which may lead to an altered functionality of the said valve prostheses, whereas in mechanical valve prostheses, the state of operation of the movable closing and opening elements, typically disks or half-disks made of pyrolytic carbon, may be jeopardized by trombo-embolic phenomena, which can be mitigated and controlled with an adequate anticoagulant therapy.

Since the number of patients with implanted cardiac systems is increasing considerably, it would be useful for the community at large to have available sensorized valve prostheses, which can interact with an external monitoring terminal, having, for example, the size and weight of a smartphone or tablet, to make it possible to check at home the state of operation of the said valve prostheses, so that a patient can go to the specialised health structure when said monitoring terminal detects an anomaly in operation of the sensorized prosthesis and issues a warning.

It is evident that such a monitoring system could improve the quality of life of patients with implanted valve prostheses, also reducing mortality of patients in the case where the said monitoring system indicates situations of alarm related to a highly probable state of deterioration of the valve prosthesis, so that the patient himself can be alerted and can go to a specialised health structure for possible early replacement of the said heart valve prosthesis before the latter is damaged.

As prior art, reference may be made to the examples cited below.

The U.S. Pat. No. 5,487,760 refers to a heart valve prosthesis of a mechanical type, equipped with a sensor of a capacitive or inductive type or a vibration sensor, for example of the piezoelectric type, connected to an electronic microcircuit set between the external structure of the valve and the material that coats the suture ring, in order to detect signals correlated to the opening and closing movement of the leaflets of the said heart valve prosthesis and also describes how to energize said internal microcircuit and how to interact therewith, through a telemetry device external to the patient. The disclosure of the patent application WO2010/062223 refers to a lead for cardiac pacing, to be inserted in the right-hand cardiac cavities or in the coronary sinus, equipped with electrodes and connected to means for measuring electrical impedance and for monitoring, through this, operation of the natural heart valves. The U.S. Pat. No. 7,643,879 describes how to sensorize a heart valve prosthesis through a physiological sensor configured for detecting the electrical signal of the heart in the proximity of a heart valve and a sensor configured for detecting haemodynamic parameters, wherein said sensor comprises a flowrate sensor for detecting the flow of the blood, or else a pressure sensor, or else a sensor for detecting deflection of the leaflets of the valve, for example of an electromagnetic, or else piezoresistive, or else piezoelectric, type or else a Hall-effect sensor, acoustic sensors, or optical sensors. Also the disclosure of the patent US2012/0296382A1 describes in a generic way a heart valve prosthesis which includes a physiological sensor and an electronic microcircuit that enables transmission of the vital physiological information detected by said sensor to means external to the patient. The U.S. Pat. No. 7,089,051 describes in a very generic way how to monitor opening of the aortic valve with a measurement of electrical impedance made between extra-valve electrodes, located in the cardiac sinus and in the great cardiac vein. The U.S. Pat. No. 5,792,194 describes a device for measuring an electrical impedance between electrodes set in the atrium and in the ventricle for measuring a useful parameter during physical activity to control cardiac stimulation (RR function) by an electrical cardiac pacing device. Also the U.S. Pat. No. 4,730,619 describes a device for regulating the electrostimulation frequency of an implanted device such as a pacemaker as a function of the variations of electrical impedance-detected in this case between electrodes set on an electro-catheter inserted within the cardiac cavity and an electrode located on the case of the said pacemaker. Finally, the U.S. Pat. No. 5,902,325 describes a cardiac-stimulation apparatus that detects the cardiac capture by means of a measurement of electrical impedance.

From the known art it may be evinced that the measurements of electrical impedance or rheographic measurements made between two or more electrodes inserted in cardiac pacing lead is a technique that has been used for more than thirty years, is by now consolidated, is easy to implement, and presents high technological reliability. So far the rheographic technique has been used basically for detecting mainly parameters (minute ventilation or atrio-ventricular impedance) for adapting pacing rate in implantable electrical cardiac pacing device (rate responsive pacing) and, when it has been used for detecting the opening movement of a natural valve, as in U.S. Pat. No. 7,089,051 considered above, it has been carried out between electrodes set in pacing leads inserted in the coronary sinus and great cardiac vein, hence obtaining, given the extravalvular position of the electrodes, a measurement of electrical impedance that is correlated to the movement of the valve leaflets but that may be markedly falsified by the variations of the volumes of blood present in the cardiac cavities and in the vessels themselves in which the measurement electrodes are inserted and by the considerable changes in shape of the cardiac muscle.

BRIEF SUMMARY

The inventor has had the intuition and the creative stimulus of verifying whether the rheographic technique referred to above could be adapted for detecting the displacements alone, which are very localised, caused by the opening and closing movement of the leaflets of a natural heart valve or of the movable opening and closing elements of an artificial valve, and the experimental tests conducted by the inventor have surprisingly shown the positive, precise, and highly reliable results that can derive from a measurement of intravalvular electrical impedance, i.e., with generation of electrical field localised within the restricted context of a heart valve prosthesis. The invention consequently proposes the use of said impedentiometric technique for detecting the movement alone of the leaflets of a natural heart valve repaired with an annuloplasty intervention or of the movable opening and closing elements of a mechanical or tissue heart valve prosthesis, or also of a tissue valve implanted with a transcatheter system, and proposes a sensorized heart valve, presenting a high technological reliability, prearranged for interacting with an external monitoring system, according to Claim 1 and to the subsequent dependent claims, which exploits the following arrangement: electrodes are set in the annular base of the prosthetic valve device for generation of an electrical field, the field lines of which traverse the section or the lumen of said annular body, on which the natural leaflets or the movable opening and closing elements of the said heart valve prosthesis cyclically move, determining variations of said electrical field that are detected through said electrodes or supplementary electrodes and that, through a dedicated electronic circuit, of an ASIC type, which may also be integrated entirely or partially in the heart valve prosthesis, are converted into variations of intravalvular electrical impedance, which present an evolution correlated to the conditions of opening and closing of the valve leaflets or of the movable elements of the implanted prosthetic valve device. The internal electronic circuit operative on the valve comprises telemetry means through which the said internal circuit can communicate with an external terminal that can carry out activation and energization of the said internal circuit and that from this detects said variations of electrical impedance or corresponding signals that it can then process and analyse for purposes of monitoring, prevention, and for other possible purposes. Said internal electronic circuit may be completely integrated in the prosthetic valve device, or else may be in part located in said prosthetic device and connected via wire to other electronic circuits set in a case subcutaneously implanted in the patient, which can likewise house said internal telemetry means for communication with the external querying terminal and which may contain an autonomous electric power supply source (see below). The circuits for processing the signal acquired by the electrodes associated to the valve prosthesis for detection of the variations of intravalvular electrical impedance may be located in said electronic circuits internal to the patient or else may be located in the external terminal.

BRIEF DESCRIPTION OF THE DRAWINGS

Further characteristics of the invention, and the advantages that derive therefrom, will emerge more clearly from the ensuing description of some preferred embodiments, illustrated purely by way of non-limiting example in the attached three plates of drawings, wherein:

FIGS. 1 and 2 are schematic and top plan views of a mechanical heart valve prosthesis with a different arrangement of the said electrodes for measuring the variations of intravalvular electrical impedance;

DETAILED DESCRIPTION

Figure 3:
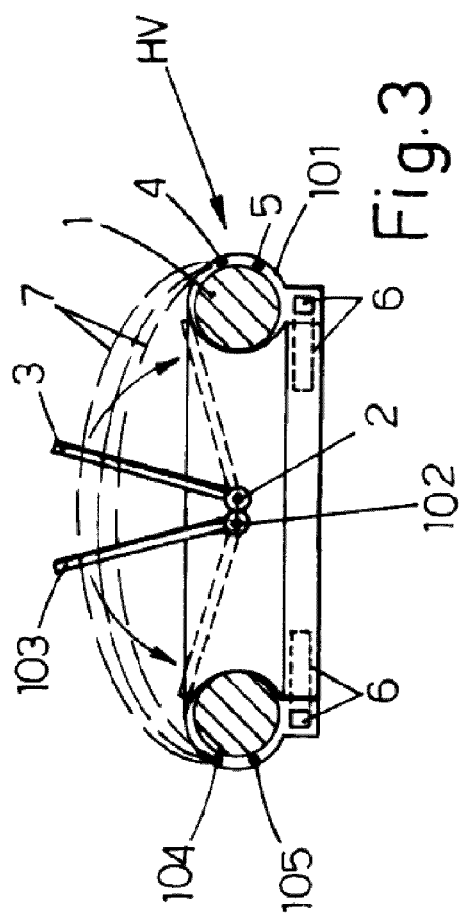
FIG. 3 illustrates schematically the heart valve prosthesis of FIG. 1 sectioned according to the line III-III.

FIGS. 1, 2, and 3 illustrate a heart valve prosthesis HV of a mechanical type, equipped with a base body 1 of an annular shape, mounted in which, with possibility of oscillation about transverse and median axes 2, 102, are movable elements 3, 103 shaped like half-disks, which during operation of the said prosthesis HV pass from the opening position, represented by a solid line, to the closing position, represented by a dashed line. For simplifying presentation of the invention, other types of heart valve prosthesis to which the improvements according to the present invention can be made are not illustrated herein, in so far as said improvements essentially concern the annular base body 1 of the prosthesis, which is present both in annuloplasty rings and in artificial heart valves proper, whether they are of a mechanical type or of a tissue type, or else of a tissue type implanted with the transcatheter technique.

According to the invention, at the moment of manufacturing of the heart valve prosthesis, integrated in said annular body 1 or on the outer surface of the coating 101 thereof, for example in the area of suture of the said annular ensemble 1, 101, are electrodes made of suitable material 4, 104 and other possible electrodes 5, 105 (see below), preferably diametrally opposed to one another and mutually aligned according to a direction substantially orthogonal to the axes 2, 102 in the case of the mechanical valve HV illustrated. The electrodes 4, 104 and 5, 105 may be located for example according to the length of the annular body 1, as shown in FIG. 1, or may be located in the said body 1 with an arrangement that is, for example, transverse, as illustrated in FIG. 2, or with an arrangement that is both transverse and longitudinal, for example with an oblique arrangement (not illustrated).

The electrodes 4, 104 and 5, 105 are connected to microelectronic circuit 6 which is also associated to the body 1 and protected in the corresponding casing 101, and said circuit 6 may be formed by one or more components however distributed along the length of the said body 1 and functionally connected together. Good results of electrical response have been obtained using four electrodes 4, 104 and 5, 105 and a corresponding quadripolar measurement, but it remains understood that, even at the expense of a greater complexity of implementation of the circuit 6, just two electrodes may be used that alternate rapidly in the function of excitation and reception (for a bipolar measurement), or three electrodes, with a common electrode for both of said functions of excitation and reception (for a tripolar measurement).

The purpose of the invention is described in what follows and is illustrated schematically in FIG. 3. The electrodes 4, 104 are supplied with an electric current I of a known and constant value so as to generate between them an electrical field 7, the field lines of which interfere with the natural leaflets of the heart valve or with the movable elements 3, 103 of the artificial heart valve prosthesis during their opening and closing movement. The variations of the electrical field produced by the cyclic movement of the natural leaflets or of the movable elements of the heart valve prosthesis are detected with a measurement of voltage V for example between the electrodes 5, 105, in order to derive, by applying Ohm's law $Z=V/I$, where I is a known and constant value, to the variations $\Delta V$ of the voltage V, the variations of electrical impedance $\Delta Z$ deriving from the opening and closing movement of the leaflets of the valve, so that it is possible to verify any malfunctioning of the sensorized valve prosthesis.

Figure 7:
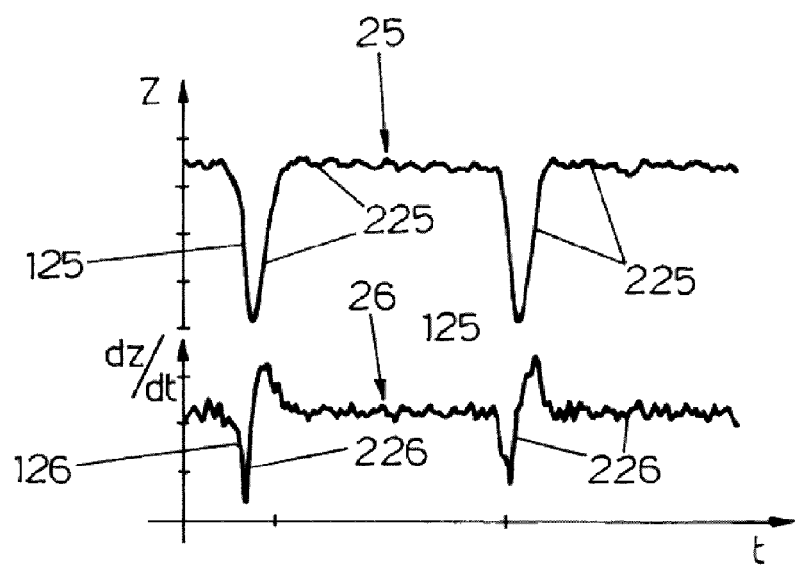
FIG. 7 illustrates the plot of the variations of intravalvular electrical impedance that can be detected with the system according to the invention, in relation with the simulated opening and closing movements of the leaflets of a sensorized heart valve prosthesis.

In the diagrams of FIG. 7, the signal 25 represents the plot in time "t" of the intravalvular-impedance signal corresponding to the movements of closing 125 and opening 225 of the leaflets of a heart valve prosthesis monitored, whereas the signal 26 appearing at the bottom is the corresponding time plot of the signal of the first derivative in time "t" of the intravalvular-impedance signal.

The technology used in the present invention is not affected by possible fibrotic growths or of pannus formations on the base 1, 101 of the heart valve prosthesis HV, which will not modify the reliability of the system in so far as said growths are traversed without presenting any substantial resistance by the lines of the electrical field 7 and by the RF electromagnetic radiations that will be mentioned hereinafter. It may thus be appreciated how the solution according to the invention is highly reliable over time, also because it does not alter in any way the morphology, dynamics, and hence functionality of the natural leaflets or of the movable closing elements of the heart valve prosthesis in the case where this is implanted.

Figure 4:
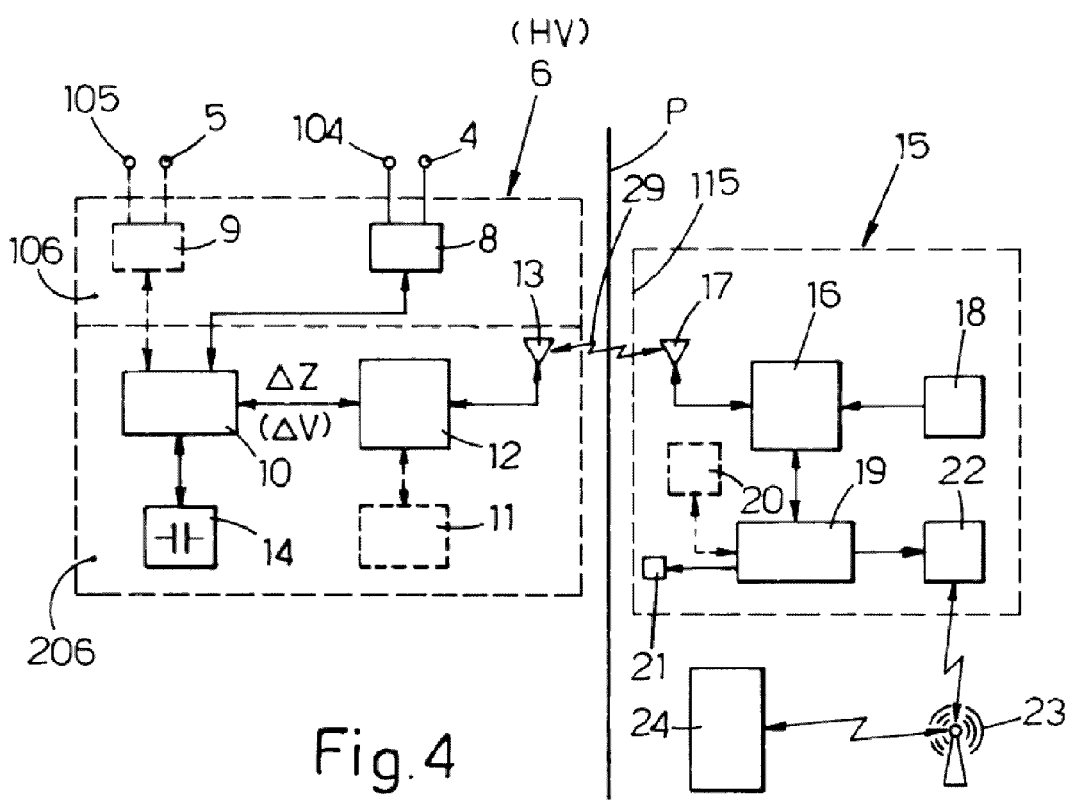
FIG. 4 illustrates a block diagram of the electronic components set within the body of the patient and of the external components for detection of the variations of intravalvular electrical impedance.

With reference to FIG. 4 a possible simplified embodiment of the microelectronic circuit 6 is now described, which comprises: an electric power supply unit 14 (see below), and a control and processing unit 10 connected to the electrodes 4, 104, and to the possible electrodes 5, 105, by means of interfaces 8 and 9 for generation of the measurement electrical current and for conditioning of the signal detected, such as amplification, filtering and the like, there being connected to the said unit 10 a possible storage unit 11 and a transceiver unit 12 with at least a corresponding antenna 13. The detailed description of the components 8, 9, and 10 is omitted in so far as the latter may be readily obtained by the person skilled in the branch on the basis of the knowledge of the known art cited in the introductory part of the present disclosure and of all those solutions that use impedance or the rheographic technique for detecting variations of the minute and/or pulmonary ventilation of a patient.

The circuit 6 can interact with a small external terminal 15, for example of the size of a smartphone or tablet, which carries inside it: a transceiver unit 16 with at least a corresponding antenna 17; an electric power supply unit 18; a processor 19; a possible storage unit 20; a unit 21 for displaying the conditions detected and possible alarm conditions; and a possible modem 22 or equivalent arrangement for connection with such a means or with an equivalent remote communication means.

Figure 5:
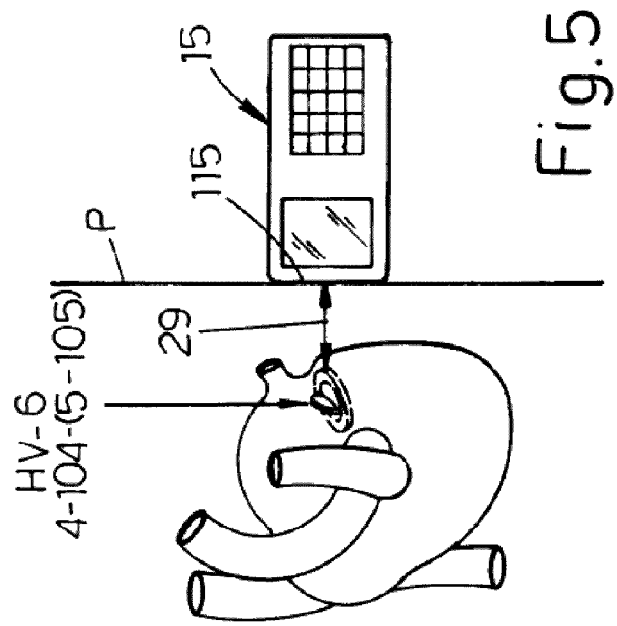
FIGS. 5 and 6 are schematic illustrations of two different possible locations of the electronic components in the body of the patient equipped with the sensorized heart valve prosthesis according to the invention.

The system of FIG. 4 functions as described in what follows. As illustrated in FIGS. 4 and 5, the terminal 15 is rested with its own dedicated end 115 on the chest P of the patient or else is set in a position sufficiently close to the patient, and from the said terminal 15 a transmission step is activated. Through the antenna 17 of the terminal 15 an electromagnetic signal 29, for example an RF signal, is irradiated and is received by the antenna 13 of the implanted system 6, said signal containing both data and the electromagnetic energy necessary for electrical charging of the unit 14, which is, for example, of a capacitive type. The microelectronic circuit 6 internal to the valve prosthesis is energized from outside, and through the unit 10 and the interface 8, and the possible interface 9, connected to the electrodes 4, 104, and to the possible electrodes 5, 105, an electrical signal that corresponds to the variations of the intravalvular electrical impedance $\Delta Z$ is detected, said data being possibly stored in the unit 11 and sent to the unit 12 switched into the transmitter function, which, through the antenna 13, transmits said data to the antenna 17 of the external unit 15, and hence to the unit 16 in receiving mode, and then the said data are sent to the processing unit 19, which analyses them, stores them in the unit 20, and communicates the outcome of the result through the unit 21, for example, by means of a display.

During execution of the said examination or at a subsequent moment, through the unit 22 and through telecommunication services 23 the data detected in the said examination may possibly be transmitted to the remote server 24 of a specialised health centre, which can use said data for further checks, for purposes of prevention and for other possible purposes.

Figure 6:
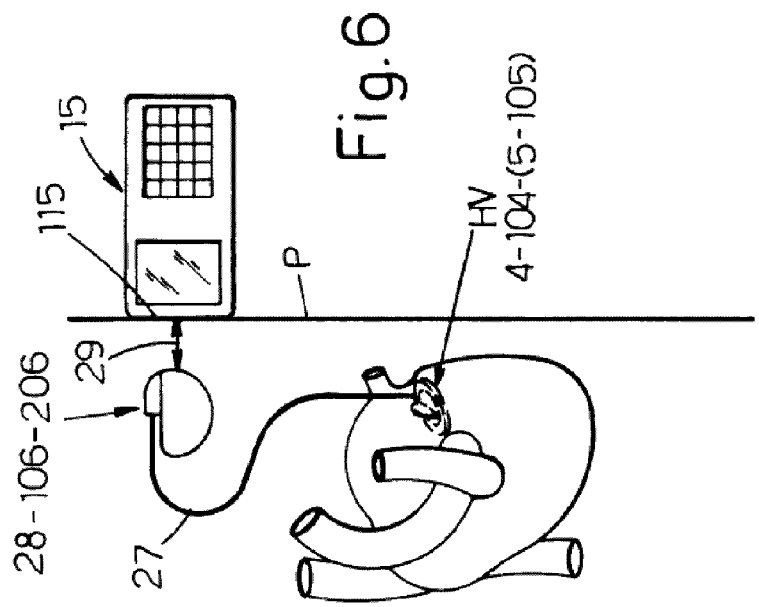

FIG. 6 illustrates a possible variant embodiment of the invention, which envisages minimizing the electronic components on board the heart valve prosthesis HV, limiting them to the essential components such as, for example, at least the two or more electrodes 4, 104 and 5, 105 of FIG. 4, connected by means of electric wires 27 (FIG. 6) to all electronic components of blocks 106 and 206 of FIG. 4, which are now housed in a hermetic container 28 implanted under the skin of the patient, similar to the housing of an implantable electrical cardiac pacing device. In this case, the component 14 of FIG. 4 may be of the type referred to above, chargeable from outside by induction, or may be replaced by an electric battery of the same type as the ones used in pacemakers, with the consequent conceivable simplifications, both as regards the implanted electronic circuit, which will be self-sufficient for the purposes of electric power supply, and as regards the external terminal 15, which will now have only to issue a command for wake-up and activation of the internal circuit and collect the data corresponding at least to the variations of the intravalvular electrical impedance.

It remains understood that the description refers to a preferred and essential embodiment of the invention, to which numerous variations and modifications may be made, in addition to the ones indicated above, aimed for example at detecting, through the variations of intravalvular electrical impedance, other parameters of the cardiac activity, for example the rate of opening and closing of the leaflets of the valve being monitored and/or other parameters indicating the clinical conditions of the implanted patient. Falling within the scope of the invention are also the variants whereby the signal linked to the variations of the intravalvular electrical impedance $\Delta Z$ is obtained from the external unit 15 by processing the raw signal of the variations of electrical field that the said unit 15 receives from the internal unit 6.

The above and all the modifications and technical equivalents, which may on the other hand be conceived by the person skilled in the branch, do not depart from the scope of the invention as described, as illustrated in figures of the three attached plates of drawings, and as claimed hereinafter. In the claims, the references appearing in brackets are purely indicative and do not limit the sphere of protection of the claims themselves.

The invention claimed is:

1. A heart valve prosthesis of any type, with internal microelectronic circuit for monitoring the motion of the natural valve leaflets or of the artificial opening and closing elements of the heart valve prosthesis, and external electronic system for telemetric monitoring of such a sensorized heart valve prosthesis, characterized in that the heart valve prosthesis comprises two or more electrodes set in the annular base body of the prosthesis itself, and comprises an internal microelectronic circuit, which is connected to electric power supply means, and provided with means for generating between said electrodes, an electrical field, the field lines of which are oriented so as to interfere with the opening and closing movement of the movable elements of said heart valve prosthesis or of the leaflets of the natural heart valve on which the prosthesis itself will be mounted, and is equipped with or connected to means for detecting the variations of said electrical field produced by the cyclic opening or closing movement of said movable elements or of said leaflets, which will be expressed as variations of intravalvular electrical impedance, and characterized in that it comprises an implanted transceiver unit with corresponding antenna for telemetric transmission of the data correlated to said variations of intravalvular electrical impedance to an external unit, which processes the collected data and uses them at least for purposes of diagnosis and prevention.

2. The heart valve prosthesis according to claim 1, wherein said internal microelectronic circuit comprises an electric power supply unit and one or more interfaces connected to said two or more electrodes and to a control and processing unit to which a possible storage unit and a transceiver unit with at least a corresponding antenna are connected.

3. The heart valve prosthesis according to claim 2, wherein all the components of the internal microelectronic circuit, in addition to the electrodes are integrated in the annular body of the said heart valve prosthesis, of whatever type it may be.

4. The heart valve prosthesis according to claim 2, wherein the two or more electrodes are integrated in the annular base body of the said prosthesis, and are electrically connected by wires to the internal electronic circuit located in a hermetic container implanted under the skin of the patient, like a hermetic housing of an electrical cardiac pacing device, it being in this case envisaged that said electric power supply unit can be charged by induction by the external unit or which can include an electric battery of the type used in implantable electrical cardiac pacing devices.

5. The heart valve prosthesis according to claim 1, wherein the external unit designed to interact with the said prosthesis has, for example, the size and shape of a smartphone or a tablet and carries inside: a transceiver unit with at least a corresponding antenna, prearranged for transmitting and receiving signals and for transmitting also the possible electromagnetic energy necessary for energizing the electric power supply unit set at the service of the internal microelectronic circuit of the prosthesis; an electric power supply unit; a processor; a possible storage unit; a unit for displaying the conditions, including alarm conditions, detected by the interaction with said microelectronic circuit of the heart valve prosthesis.

6. The heart valve prosthesis according to claim 5, wherein said external unit comprises or is prearranged for connection to a modem or equivalent means that enable transmission of the data detected by the external unit itself to the server of a specialised medical centre, which can use said data for further checks and for other purposes, also of prevention and statistics.

7. The heart valve prosthesis according to claim 1, wherein the means for processing the signal corresponding to the variations of intravalvular electrical impedance may be provided in the external unit, which receives from the internal unit the raw signal corresponding to the intravalvular electrical impedance detected via the two or more electrodes and produced by the movement of the valvular leaflets or by the movable opening and closing elements of the sensorized heart valve prosthesis.

8. The heart valve prosthesis according to claim 1, wherein the external unit is equipped with means for detecting through the variations of intravalvular electrical impedance, other parameters of the cardiac activity, such as for example the rate of opening and closing of the movable opening and closing elements of the heart valve prosthesis being monitored and/or also other physiological parameters indicating the clinical conditions of the implanted patient.

* * * * *